United States Patent
Walker et al.

(10) Patent No.: US 10,800,727 B2
(45) Date of Patent: Oct. 13, 2020

(54) METHOD FOR PRODUCTION OF METHYL METHACRYLATE BY OXIDATIVE ESTERIFICATION USING A HETEROGENEOUS CATALYST

(71) Applicants: Rohm and Haas Company, Collegeville, PA (US); Dow Global Technologies LLC, Midland, MI (US)

(72) Inventors: Justin Walker, Midland, MI (US); Kirk W. Limbach, Dresher, PA (US); Jeffrey Herron, Midland, MI (US)

(73) Assignees: Rohm and Haas Company, Collegeville, PA (US); Dow Global Technologies LLC, Midland, MI (US)

( * ) Notice: Subject to any disclaimer, the term of this patent is extended or adjusted under 35 U.S.C. 154(b) by 0 days.

(21) Appl. No.: 16/632,561

(22) PCT Filed: Jun. 25, 2018

(86) PCT No.: PCT/US2018/039240
§ 371 (c)(1),
(2) Date: Jan. 21, 2020

(87) PCT Pub. No.: WO2019/022891
PCT Pub. Date: Jan. 31, 2019

(65) Prior Publication Data
US 2020/0157037 A1    May 21, 2020

Related U.S. Application Data

(60) Provisional application No. 62/538,242, filed on Jul. 28, 2017.

(51) Int. Cl.
| | | |
|---|---|---|
| *C07C 67/44* | (2006.01) | |
| *B01J 8/10* | (2006.01) | |
| *B01J 21/04* | (2006.01) | |
| *B01J 23/52* | (2006.01) | |
| *B01J 23/644* | (2006.01) | |
| *B01J 35/02* | (2006.01) | |
| *B01J 35/08* | (2006.01) | |

(52) U.S. Cl.
CPC ............. *C07C 67/44* (2013.01); *B01J 8/10* (2013.01); *B01J 21/04* (2013.01); *B01J 23/52* (2013.01); *B01J 23/6447* (2013.01); *B01J 35/023* (2013.01); *B01J 35/08* (2013.01); *B01J 2208/0084* (2013.01); *B01J 2208/00867* (2013.01)

(58) Field of Classification Search
CPC .......... C07C 67/39; C07C 45/75; C07C 69/54
See application file for complete search history.

(56) References Cited

U.S. PATENT DOCUMENTS

| | | |
|---|---|---|
| 4,249,019 A | 2/1981 | Tamura et al. |
| 4,518,796 A | 5/1985 | Aoshima et al. |
| 4,520,125 A | 5/1985 | Baer et al. |
| 5,892,102 A | 4/1999 | Mikami et al. |
| 5,969,178 A | 10/1999 | Okamoto et al. |
| 6,040,472 A | 3/2000 | Yamamatsu et al. |
| 6,228,800 B1 | 5/2001 | Yamaguchi et al. |
| 7,326,806 B2 | 2/2008 | Hayashi et al. |
| 8,461,373 B2 | 6/2013 | Suzuki et al. |
| 8,614,349 B2 | 12/2013 | Yokota et al. |
| 9,511,351 B2 | 12/2016 | Feaviour |
| 9,617,199 B2 | 4/2017 | Krill et al. |
| 2016/0068464 A1* | 3/2016 | Krill ................. C07C 45/75 560/208 |
| 2016/0251301 A1 | 9/2016 | Krill et al. |
| 2016/0280628 A1 | 9/2016 | Krill et al. |
| 2019/0099731 A1* | 4/2019 | Lygin .................. B01J 8/226 |

FOREIGN PATENT DOCUMENTS

| | | |
|---|---|---|
| CN | 1931824 A | 3/2007 |
| EP | 0890569 A1 | 1/1999 |
| WO | 2017084969 | 5/2017 |

* cited by examiner

*Primary Examiner* — Jafar F Parsa
(74) *Attorney, Agent, or Firm* — Brian L. Mutschler

(57) ABSTRACT

A method for preparing methyl methacrylate from methacrolein and methanol; said method comprising contacting in a reactor a mixture comprising methacrolein, methanol and oxygen with a catalyst bed of heterogeneous catalyst comprising a support and a noble metal, wherein mass transfer rate of oxygen in hour$^{-1}$ divided by space-time yield in moles methyl methacrylate/kg·catalyst hour in the catalyst bed is at least 20.

10 Claims, No Drawings

METHOD FOR PRODUCTION OF METHYL METHACRYLATE BY OXIDATIVE ESTERIFICATION USING A HETEROGENEOUS CATALYST

BACKGROUND OF THE INVENTION

The invention relates to a method for preparing methyl methacrylate from methacrolein and methanol using a heterogeneous catalyst.

Heterogeneous catalysts having noble metals concentrated in an outer region of the catalyst have been used in oxidative esterification reactions, see, e.g., U.S. Pat. No. 6,228,800. However, there is a need for a process which can provide improved selectivity.

SUMMARY OF THE INVENTION

The present invention is directed to a method for preparing methyl methacrylate from methacrolein and methanol; said method comprising contacting in a reactor a mixture comprising methacrolein, methanol and oxygen with a catalyst bed of heterogeneous catalyst comprising a support and a noble metal, wherein mass transfer rate of oxygen in hour$^{-1}$ divided by space-time yield in moles methyl methacrylate/kg·catalyst hour in the catalyst bed is at least 25 kg catalyst/mole methyl methacrylate.

DETAILED DESCRIPTION OF THE INVENTION

All percentage compositions are weight percentages (wt %), and all temperatures are in ° C., unless otherwise indicated. A noble metal is any of gold, platinum, iridium, osmium, silver, palladium, rhodium and ruthenium. More than one noble metal may be present in the catalyst, in which case the limits apply to the total of all noble metals. The "catalyst center" is the centroid of the catalyst particle, i.e., the mean position of all points in all coordinate directions. A diameter is any linear dimension passing through the catalyst center and the average diameter is the arithmetic mean of all possible diameters. The aspect ratio is the ratio of the longest to the shortest diameters.

Oxygen mass transfer rate, $k_L a$ may be calculated for a continuous stirred tank reactor (CSTR) by the following equation for reactors whose liquid height:tank inner diameter ratio, H/T is at least 1:

$$k_L a = 0.46 * \varepsilon_m^{0.41} * v_{sg}^{0.49}$$

wherein $\varepsilon_m$ is power per unit mass and $v_{sg}$ is superficial gas velocity, provided that $1 < H/T < 2.4$, $0 < \varepsilon_m < 1.3 \text{ W·kg}^{-1}$ and $0 < v_{sg} < 0.014 \text{ ms}^{-1}$. $\varepsilon_m$ is calculated from torque times rotation rate of an impeller in the reactor divided by liquid mass. $v_{sg}$ is the volume flow rate of gas in m$^3$/s divided by the interior cross-sectional area of the reactor.

Preferably, mass transfer rate of oxygen in hour$^{-1}$ divided by space-time yield in moles methyl methacrylate/kg·catalyst hour in the catalyst bed is at least 27, preferably at least 29, preferably at least 30; preferably no greater than 500, preferably no greater than 250, preferably no greater than 200. Preferably, superficial velocity of liquid through the catalyst bed is from 0.1 to 100 mm/s; preferably at least 1 mm/s, preferably at least 2 mm/s, preferably at least 3 mm/s, preferably at least 5 mm/s; preferably no greater than 50 mm/s, preferably no greater than 35 mm/s, preferably no greater than 25 mm/s. Preferably, stirred tank reactors have at least one impeller. Preferably, the linear tip speed of the impeller is from 0.1 to 10 m/s; preferably at least 0.2 m/s, preferably at least 0.5 m/s, preferably at least 1 m/s, preferably at least 2 m/s; preferably no greater than 8 m/s, preferably no greater than 6 m/s. Preferably, the specific energy dissipation, c is from 0 to 5 W/kg; preferably at least 0.5 W/kg, preferably at least 1.0 W/kg; preferably no more than 4 W/kg, preferably no more than 3 W/kg, preferably no more than 2 W/kg. Preferably, H/T for the reactor is at least 1.0, preferably at least 1.2, preferably at least 1.4; preferably no greater than 5, preferably no greater than 4, preferably no greater than 3, preferably no greater than 2.

Preferably, oxygen concentration at a reactor outlet is from 0.5 to 7.5 mol %; preferably at least 1 mol %, preferably at least 1.5 mol %, preferably at least 2 mol %; preferably no greater than 7 mol %, preferably no greater than 6.5 mol %.

Preferably, the support is a particle of an oxide material; preferably γ-, δ-, or θ -alumina, silica, magnesia, titania, zirconia, hafnia, vanadia, niobium oxide, tantalum oxide, ceria, yttria, lanthanum oxide or a combination thereof; preferably γ-, δ-, or θ-alumina. Preferably, in portions of the catalyst comprising noble metal, the support has a surface area greater than 10 m$^2$/g, preferably greater than 30 m$^2$/g, preferably greater than 50 m$^2$/g, preferably greater than 100 m$^2$/g, preferably greater than 120 m$^2$/g. In portions of the catalyst which comprise little or no noble metal, the support may have a surface area with less than 50 m$^2$/g, preferably less than 20 m$^2$/g.

Preferably, the aspect ratio of the catalyst particle is no more than 10:1, preferably no more than 5:1, preferably no more than 3:1, preferably no more than 2:1, preferably no more than 1.5:1, preferably no more than 1.1:1. Preferred shapes for the catalyst particle include spheres, cylinders, rectangular solids, rings, multi-lobed shapes (e.g., cloverleaf cross section), shapes having multiple holes and "wagon wheels;" preferably spheres. Irregular shapes may also be used.

Preferably, at least 90 wt % of the noble metal(s) is in the outer 70% of catalyst volume (i.e., the volume of an average catalyst particle), preferably the outer 60% of catalyst volume, preferably the outer 50%, preferably the outer 40%, preferably the outer 35%, preferably in the outer 30%, preferably in the outer 25%. Preferably, the outer volume of any particle shape is calculated for a volume having a constant distance from its inner surface to its outer surface (the surface of the particle), measured along a line perpendicular to the outer surface. For example, for a spherical particle the outer x % of volume is a spherical shell whose outer surface is the surface of the particle and whose volume is x % of the volume of the entire sphere. Preferably, at least 95 wt % of the noble metal is in the outer volume of the catalyst, preferably at least 97 wt %, preferably at least 99 wt %. Preferably, at least 90 wt % (preferably at least 95 wt %, preferably at least 97 wt %, preferably at least 99 wt %) of the noble metal(s) is within a distance from the surface that is no more than 30% of the catalyst diameter, preferably no more than 25%, preferably no more than 20%, preferably no more than 15%, preferably no more than 10%, preferably no more than 8%. Distance from the surface is measured along a line which is perpendicular to the surface.

Preferably, the noble metal is gold or palladium, preferably gold.

Preferably, the average diameter of the catalyst particle is at least 30 microns, preferably at least 60 microns, preferably at least 100 microns, preferably at least 200 microns, preferably at least 300 microns, preferably at least 400 microns, preferably at least 500 microns, preferably at least 600 microns, preferably at least 700 microns, preferably at least 800 microns; preferably no more than 30 mm, preferably no more than 20 mm, preferably no more than 10 mm, preferably no more than 5 mm, preferably no more than 4 mm. The average diameter of the support and the average diameter of the final catalyst particle are not significantly different.

Preferably, the amount of noble metal as a percentage of the noble metal and the support is from 0.2 to 5 wt %, preferably at least 0.5 wt %, preferably at least 0.8 wt %, preferably at least 1 wt %, preferably at least 1.2 wt %; preferably no more than 4 wt %, preferably no more than 3 wt %, preferably no more than 2.5 wt %.

Preferably, the catalyst is produced by precipitating the noble metal from an aqueous solution of noble metal salt in the presence of the support. In one embodiment of the invention, the catalyst is produced by incipient wetness in which an aqueous solution of a suitable noble metal precursor salt is added to a porous inorganic oxide such that the pores are filled with the solution and the water is then removed by drying. The resulting material is then converted into a finished catalyst by calcination, reduction, or other pre-treatments known to those skilled in the art to decompose the noble metal salts into metals or metal oxides. Preferably, a $C_2$-$C_{18}$ thiol comprising at least one hydroxyl or carboxylic acid substituent is present in the solution. Preferably, the $C_2$-$C_{18}$ thiol comprising at least one hydroxyl or carboxylic acid substituent has from 2 to 12 carbon atoms, preferably 2 to 8, preferably 3 to 6. Preferably, the thiol compound comprises no more than 4 total hydroxyl and carboxylic acid groups, preferably no more than 3, preferably no more than 2. Preferably, the thiol compound has no more than 2 thiol groups, preferably no more than one. If the thiol compound comprises carboxylic acid substituents, they may be present in the acid form, conjugate base form or a mixture thereof. Especially preferred thiol compounds include thiomalic acid, 3-mercaptopropionic acid, thioglycolic acid, 2-mercaptoethanol and 1-thioglycerol, including their conjugate bases.

In one embodiment of the invention, the catalyst is produced by deposition precipitation in which a porous inorganic oxide is immersed in an aqueous solution containing a suitable noble metal precursor salt and that salt is then made to interact with the surface of the inorganic oxide by adjusting the pH of the solution. The resulting treated solid is then recovered (e.g. by filtration) and then converted into a finished catalyst by calcination, reduction, or other pre-treatments known to those skilled in the art to decompose the noble metal salts into metals or metal oxides.

The process for producing methyl methacrylate (MMA) comprises treating methacrolein with methanol and oxygen in an oxidative esterification reactor (OER) containing a catalyst bed. The catalyst particles in the catalyst bed typically are held in place by solid walls and by screens or catalyst support grids. In some configurations, the screens or grids are on opposite ends of the catalyst bed and the solid walls are on the side(s), although in some configurations the catalyst bed may be enclosed entirely by screens. Preferred shapes for the catalyst bed include a cylinder, a rectangular solid and a cylindrical shell; preferably a cylinder. The OER further comprises a liquid phase comprising methacrolein, methanol and MMA and a gaseous phase comprising oxygen. The liquid phase may further comprise byproducts, e.g., methacrolein dimethyl acetal (MDA) and methyl isobutyrate (MIB). Preferably, the liquid phase is at a temperature from 40 to 120° C.; preferably at least 50° C., preferably at least 60° C.; preferably no more than 110° C., preferably no more than 100° C. Preferably, the catalyst bed is at a pressure from 0 to 2000 psig (101.3 to 13890.8 kPa); preferably no more than 2000 kPa, preferably no more than 1500 kPa. Preferably, pH in the catalyst bed is from 4 to 10; preferably at least 5, preferably at least 5.5; preferably no greater than 9, preferably no greater than 8, preferably no greater than 7.5. Preferably, the catalyst bed is in a tubular continuous reactor or a continuous stirred tank reactor, preferably a tubular continuous reactor. Preferably, the catalyst bed further comprises oxygen gas.

In one embodiment of the invention, the catalyst bed is situated within a continuous stirred tank reactor (CSTR) such that fluid flow may occur through the catalyst bed. Preferably, the reactor comprises a stack, which is a vertical solid partition having an inside and an outside (i.e., its cross-section perpendicular to the height is a continuous closed curve), allowing fluid flow upward on one side of the stack (e.g., inside or outside) and downward on the other side. In a preferred embodiment the catalyst bed is in the shape of a substantially cylindrical shell located between the stack and the reactor walls. The stack may be a cylindrical shell (cylinder with a cylindrical hole), a rectangular shell or a more complex shape, e.g., a shape derived from a cylindrical shell by flaring the sides outward (toward the reactor walls) at the ends or a shape having an outer or inner surface of a cylindrical shell but with tapering on the other surface to produce a variable thickness; preferably a cross section of the stack perpendicular to the height consists of two or more concentric circles. Preferably, the stack is centered in the reactor. Preferably, the stack is stationary relative to the reactor walls. Preferably, the long dimension of the stack is from 30 to 90% of the long dimension of the reactor, preferably from 40 to 75%. Preferably, the maximum cross-section diameter of the stack is from 40 to 90% of the diameter of the reactor, preferably at least 45%, preferably at least 50%, preferably no more than 85%, preferably no more than 80%. In a preferred embodiment in which the reactor is a continuous stirred tank reactor (CSTR), the height of the stack is from 30 to 80% of the height of the reactor; preferably at least 40%, preferably no more than 75%, preferably no more than 70%. In a CSTR, preferably the height of the catalyst bed is from 30 to 90% of the height of the stack, preferably at least 40%, preferably no more than 80%. Preferably, the sides of the catalyst bed are in contact with the stack. Preferably, the CSTR is configured with the catalyst bed between the stack and the reactor walls with liquid flow downward inside the stack and upward through the catalyst bed. Preferably gaseous reactants and inert (oxygen, nitrogen, carbon dioxide) rise upward through the catalyst bed.

Preferably, the contents of the reactor are mixed, either by at least one impeller or static mixing device or by jet mixing; preferably, a static mixing device. Preferably, impellers are on a shaft which passes through the center of the catalyst bed.

The OER typically produces MMA, along with methacrylic acid and unreacted methanol. Preferably, methanol and methacrolein are fed to the reactor containing the catalyst bed in a methanol:methacrolein molar ratio from 1:10 to 100:1, preferably from 1:2 to 1:20, preferably from 1:1 to 10:1. Preferably, the catalyst bed further comprises inert materials above and below the catalyst particles. Preferred inert materials include, e.g., alumina, clay, glass, silica carbide and quartz. Preferably, the inert materials have an average diameter equal to or greater than that of the catalyst. Preferably, the reaction products are fed to a methanol recovery distillation column which provides an overhead stream rich in methanol and methacrolein; preferably this stream is recycled back to the OER. The bottoms stream from the methanol recovery distillation column comprises MMA, MDA, methacrylic acid, salts and water. In one embodiment of the invention, MDA is hydrolyzed in a medium comprising MMA, MDA, methacrylic acid, salts and water. MDA may be hydrolyzed in the bottoms stream from a methanol recovery distillation column; said stream comprising MMA, MDA, methacrylic acid, salts and water. In another embodiment, MDA is hydrolyzed in an organic phase separated from the methanol recovery bottoms stream. It may be necessary to add water to the organic phase to ensure that there is sufficient water for the MDA hydrolysis; these amounts may be determined easily from the composition of the organic phase. The product of the MDA hydrolysis reactor is phase separated and the organic phase passes through one or more distillation columns to produce MMA product and light and/or heavy byproducts. In another embodiment, hydrolysis could be conducted within the distillation column itself.

EXAMPLES

Examples of the effect of $k_La$/STY on MIB level are provided below. The examples demonstrate that at $k_La$/STY less than 20 kg catalyst/mole MMA the mass transfer of oxygen is insufficient to reduce MIB to acceptable process levels.

Example 1

A series of runs was conducted in which 20 wt % methacrolein, 200 ppm inhibitor, and a balance of methanol were fed to a ⅜" (9.5 mm) stainless steel tubular reactor containing a short front section of silica carbide followed by 10 g of catalyst. The catalyst consisted of 1.5 wt % Au on a Norpro 1 mm diameter high-surface-area alumina spherical support, with the gold concentrated in a narrow region near the surface of the support. Air or a gas containing 8% oxygen in nitrogen were also feed to the reactor. The reactor was operated at 60° C. and 160 psig (1200 kPa). The product of the reactor was sent to a liquid-vapor separator and the vapor was sent to a condenser with liquid return. A portion of the product stream from this separator was recycled in one case to the reactor inlet and combined with the feed entering the reactor. Results are described in the table below. MIB is reported in ppm on a 100% MMA product basis.

| kLa/STY (kg catalyst/ mole MMA) | MIB/MMA (ppm) |
| --- | --- |
| 32.5 | 460 |
| 38.7 | 480 |
| 15.1 | 600 |

| Prod MMA (%) | Conv (%) | MIB (ppm) | Feed (g/hr) | Recycle (g/hr) | Vent O₂ (%) | Gas (SCCM) | Gas Type |
| --- | --- | --- | --- | --- | --- | --- | --- |
| 97.8 | 75.8 | 460 | 20 | 0 | 4 | 450 | 8% O₂ |
| 97.8 | 62.9 | 480 | 20 | 180 | 4 | 380 | 8% O₂ |
| 97.9 | 15.5 | 600 | 200 | 0 | 4 | 190 | AIR |

Example 2

A series of runs was conducted in which 20 wt % methacrolein, 200 ppm inhibitor, and a balance of methanol were fed to a 300 ml stainless steel continuous stirred tank reactor which had two 45 degree pitch blade turbines turning at various RPM from 600 to 1200. The reactor contained approximately 125 g of liquid and 20 g of catalyst, making for a 145 g slurry. The catalyst consisted of 5 wt % Pd, 2 wt % Bi, and 1 wt % Sb on a slurry size (mostly less than 100 micron diameter) alumina support material. Air was also feed to the reactor at 85 to 100 sccm. The reactor was operated at 80° C. and 60 psig (510 kPa). A solution of 1 wt % sodium methoxide was fed to the reactor to maintain the pH at 6.5. The reactor was equipped with a condenser having a liquid return. Results are described in the table below. MIB is reported in ppm on a 100% MMA product basis.

| kLa/STY (kg catalyst/ mole MMA) | MIB/MMA (ppm) |
| --- | --- |
| 21.0 | 2500 |
| 24.4 | 1000 |
| 25.9 | 650 |
| 34.6 | 450 |
| 46.8 | 380 |

| Run Hours (hrs) | RPM | O₂ in Headspace (%) | Air rate (sccm) | MIB in Product (ppm) | MMA Selectivity (%) |
| --- | --- | --- | --- | --- | --- |
| 230 | 600 | 1.0 | 85 | 2500 | 84 |
| 292 | 700 | 0.5 | 100 | 1000 | 89 |
| 317 | 800 | 0.3 | 100 | 650 | 81 |
| 349 | 900 | 0.2 | 100 | 450 | 87 |
| 386 | 1200 | 0 | 100 | 380 | 84 |

Predictive Model

Rate law expressions for the various chemical reactions in the system were derived based on a regression of laboratory and pilot plant data, and utilized to construct a predictive model for a CSTR or high-recycle tubular continuous reactor in ASPEN. This model is capable of predicting extent of reaction, byproduct formation, and the like in response to variations in process conditions. This model was used to predict MIB formation over a broad range of $k_La$ and STY values, the results of which are included as a comparison to the laboratory data.

| kLa/STY (kg catalyst/ mol MMA) | MIB/MMA (ppm) |
| --- | --- |
| 10.4 | 8616 |
| 16.4 | 4657 |
| 22.0 | 2352 |
| 24.9 | 1637 |
| 27.8 | 1133 |
| 30.9 | 794 |
| 34.0 | 579 |
| 37.2 | 454 |
| 53.8 | 400 |
| 67.0 | 385 |

The invention claimed is:
1. A method for preparing methyl methacrylate from methacrolein and methanol; said method comprising contacting in a reactor a mixture comprising methacrolein, methanol and oxygen with a catalyst bed of heterogeneous catalyst comprising a support and a noble metal, wherein mass transfer rate of oxygen in hour$^{-1}$ divided by space-time yield in moles methyl methacrylate/kg·catalyst hour in the catalyst bed is at least 25 kg catalyst/mole methyl methacrylate.

2. The method of claim 1 in which the catalyst bed is at a temperature from 40 to 120° C.

3. The method of claim 2 in which the catalyst has an average diameter from 400 microns to 10 mm.

4. The method of claim 3 in which the noble metal is selected from the group consisting of gold and palladium.

5. The method of claim 4 in which pH in the catalyst bed is from 4 to 8.

6. The method of claim 5 in which mass transfer rate of oxygen in $sec^{-1}$ divided by space-time yield in moles methyl methacrylate/kg·catalyst hour in the catalyst bed is at least 30 kg catalyst/mole methyl methacrylate.

7. The method of claim 6 in which the reactor is a continuous tubular reactor.

8. The method of claim 6 in which the reactor is a continuous stirred tank reactor.

9. The method of claim 8 in which the continuous stirred tank reactor comprises a solid baffle which allows liquid flow through the catalyst bed in one direction and height of the solid baffle is from 30 to 80% of height of the reactor.

10. The method of claim 9 in which height of liquid in the reactor divided by inside diameter of the reactor is from 1.2 to 2.2.

\* \* \* \* \*